US00PP20140P2

(12) United States Plant Patent
Shiobara

(10) Patent No.: US PP20,140 P2
(45) Date of Patent: Jun. 30, 2009

(54) ***HYDRANGEA* PLANT NAMED 'DANCING ANGEL'**

(50) Latin Name: *Hydrangea macrophylla*
Varietal Denomination: Dancing Angel

(76) Inventor: Shigeo Shiobara, 91, Shimonodo, Honjo-shi, Saitama (JP)

( * ) Notice: Subject to any disclaimer, the term of this patent is extended or adjusted under 35 U.S.C. 154(b) by 0 days.

(21) Appl. No.: 12/080,552

(22) Filed: Apr. 3, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—S. B. McCormick
(74) *Attorney, Agent, or Firm*—C. A. Whealy

(57) ABSTRACT

A new and distinct cultivar of *Hydrangea* plant named 'Dancing Angel', characterized by its upright and mounded plant habit; strong roots and stems; strong and dark green-colored leaves that are dark yellow and purple-variegated in the autumn; and large mophead-type inflorescences with pink and red purple bi-colored flowers.

2 Drawing Sheets

Botanical designation: *Hydrangea macrophylla.*
Cultivar denomination: 'Dancing Angel'.

BACKGROUND OF THE INVENTION

The present invention relates to a new and distinct cultivar of *Hydrangea,* botanically known as *Hydrangea macrophylla* and hereinafter referred to by the name 'Dancing Angel'.

The new *Hydrangea* is a naturally-occurring branch mutation of the *Hydrangea macrophylla* cultivar Pink Candy, not patented. The cultivar Dancing Angel was discovered and selected by the Inventor in April, 2000 from within a population of plants of the parent cultivar in a controlled environment in Honjo-shi, Saitama Prefecture, Japan.

Asexual reproduction of the new cultivar by softwood cuttings in Honjo-shi, Saitama Prefecture, Japan since June, 2000 has shown that the unique features of this new *Hydrangea* plant are stable and reproduced true to type in successive generations of asexual reproduction.

SUMMARY OF THE INVENTION

The cultivar Dancing Angel has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Dancing Angel'. These characteristics in combination distinguish 'Dancing Angel' as a new and distinct cultivar of *Hydrangea:*

1. Upright and mounded plant habit.
2. Strong roots and stems.
3. Strong and dark green-colored leaves that are dark yellow and purple-variegated in the autumn.
4. Large mophead-type inflorescences with pink and red purple bi-colored flowers.

Plants of the new *Hydrangea* differ primarily from plants of the parent, the cultivar Pink Candy, in foliage and flower color as plants of the cultivar Pink Candy do not have variegated foliage in the autumn and have solid pink-colored flowers.

Plants of the new *Hydrangea* can be compared to plants of the cultivar Kumiko, disclosed in U.S. Plant Pat. No. 6,924. Plants of the new *Hydrangea* differ primarily from plants of the cultivar Kumiko in the foliage and flower color as plants of the cultivar Kumiko do not have variegated foliage in the autumn and have purple pink-colored flowers. In addition, plants of the new *Hydrangea* are more compact and have smaller leaves and flowers than plants of the cultivar Kumiko.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph on the first sheet comprises a side perspective view of a typical flowering plant of 'Dancing Angel' grown in a container.

The photograph on the second sheet is a top perspective view of a typical plant of 'Dancing Angel' during the autumn after the flowers have abscised showing the variegated foliage.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown in Honjo-shi, Saitama Prefecture, Japan in a polyethylene-covered greenhouse and under conditions which closely approximate commercial production conditions. During the production of the plants, day temperatures ranged from 6° C. to 35° C., night temperatures ranged from −3° C. to 27° C. and light levels ranged from 30,000 lux to 100,000 lux.

Plants of the new *Hydrangea* were about one year old when the photographs and description were taken.

Botanical description: *Hydrangea macrophylla* cultivar Dancing Angel.

Parentage: Naturally-occurring branch mutation of the *Hydrangea macrophylla* cultivar Pink Candy, not patented.

Propagation:

*Type cutting.*—Softwood.

*Time to initiate roots, summer.*—About 15 days at 35° C. soil temperature.

*Time to initiate roots, winter.*—About 20 days at 18° C. soil temperature.

*Time to produce a rooted young plant, summer.*—About 25 days at 30° C. soil temperature.

*Time to produce a rooted young plant, winter.*—About 30 days at 18° C. soil temperature.

*Root description.*—Medium in thickness, fleshy; color, 11D.

*Rooting habit.*—Moderate branching; moderately dense.

Plant description:

*Form/growth habit.*—Perennial shrub. Upright and outwardly spreading plant habit; mounding inverted triangle. Moderately vigorous growth habit.

*Plant height.*—About 35 cm.

*Plant diameter or area of spread.*—About 40 cm.

*Branching habit.*—Moderately branching with about ten primary lateral branches developing per plant.

*Lateral branches.*—Length: About 16 cm. Diameter: About 7 mm. Internode length: About 4 cm. Texture: Smooth, glabrous. Strength: Strong. Color: Close to 143B.

Foliage description:

*Arrangement.*—Opposite, simple.

*Length.*—About 10.5 cm.

*Width.*—About 7.8 cm.

*Shape.*—Elliptic, elongated.

*Apex.*—Acuminate.

*Base.*—Acute.

*Margin.*—Lobed.

*Texture, upper and lower surfaces.*—Smooth, glabrous.

*Venation pattern.*—Pinnate.

*Color.*—Developing foliage, upper surface: Close to 137A. Developing foliage, lower surface: Close to 138B. Fully expanded foliage, upper surface: Close to 137A; occasionally at the marginal lobes, close to 59A; venation, close to 146D. Fully expanded foliage, lower surface: Close to 138B; venation, close to 146D. Autumn foliage, upper surface: Close to 17D; random streaks, spots and splotches, close to 187A. Autumn foliage, lower surface: Close to 192D; random streaks, spots and splotches, close to 77D.

*Petiole.*—Length: About 1.8 cm. Diameter: About 3 mm. Texture, upper and lower surfaces: Smooth, glabrous. Color, upper and lower surfaces: Close to 146C.

Flower description:

*Flower type and habit.*—Single sterile and fertile flowers arranged on terminal mophead-type panicles. Flowers face upright or outwardly. Flowers not fragrant.

*Natural flowering season.*—Early June in Japan.

*Flower longevity, fertile flowers.*—Flowers last about 25 days on the plant; flowers persistent.

*Flower longevity, sterile flowers.*—Flowers last about one month on the plant; flowers persistent.

*Quantity of flowers.*—Freely flowering; about 88 fertile flowers and about 120 sterile flowers per panicle.

*Panicle height.*—About 8 cm.

*Panicle diameter.*—About 17 cm.

*Flower diameter, fertile flowers.*—About 6 mm.

*Flower length, fertile flowers.*—About 3 mm.

*Flower depth (height), fertile flowers.*—About 5 mm.

*Flower diameter, sterile flowers.*—About 5.5 cm.

*Flower length, sterile flowers.*—About 3 cm.

*Flower depth (height), sterile flowers.*—About 1 cm.

*Flower buds, fertile flowers.*—Length: About 2.5 mm. Diameter: About 2.5 mm. Shape: Spherical. Color: Close to 155A.

*Flower buds, sterile flowers.*—Length: About 1.5 mm. Diameter: About 1.5 mm. Shape: Spherical. Color: Close to 147D.

*Petals, fertile flowers.*—Arrangement: Five in a single whorl. Length: About 3 mm. Width: About 2 mm. Shape: Ovate. Apex: Broadly acute. Base: Acute. Margin: Entire. Texture, upper surface: Smooth, glabrous. Texture, lower surface: Rough, glabrous. Color: When opening and fully opened, upper surface: Close to 56A to 56B; towards the base and margin, close to 65C. When opening and fully opened, lower surface: Close to 56A to 56B; towards the base and margin, close to 65C.

*Petals, sterile flowers.*—Arrangement: Four in a single whorl. Length: About 3 mm. Width: About 3.2 mm. Shape: Roughly ovate. Apex: Broadly acute. Base: Rounded. Margin: Entire; partially lobed. Texture, upper and lower surfaces: Smooth, glabrous. Color: When opening, upper surface: Close to 62B; random sectors and stripes, close to 67A. When opening, lower surface: Close to 62C; random sectors and stripes, close to 63A. Fully opened, upper surface: Close to 62A; random sectors and stripes, close to 63A. Color becoming closer to 62C with development. Fully opened, lower surface: Close to 62C; random sectors and stripes, close to 63A. Color becoming closer to 65C with development.

*Sepals, fertile flowers.*—Quantity per flower: Five in a single whorl. Length: About 0.5 mm. Width: About 1.5 mm. Shape: Lanceolate. Apex: Acute. Base: Roughly obtuse. Margin: Entire. Texture, upper and lower surfaces: Smooth, glabrous. Color, upper and lower surfaces: Close to 9D.

*Sepals, sterile flowers.*—Quantity per flower: Five in a single whorl. Length: About 2 mm. Width: About 1 mm. Shape: Elliptic. Apex: Acute. Base: Rounded. Margin: Entire. Texture, upper and lower surfaces: Smooth, glabrous. Color, upper and lower surfaces: Close to 76D.

*Pedicels, fertile flowers.*—Angle: Mostly erect. Strength: Moderately strong. Length: About 4.5 cm. Diameter: About 1 mm. Texture: Smooth, glabrous. Color: Close to 69B.

*Pedicels, sterile flowers.*—Angle: Mostly erect. Strength: Moderately strong. Length: About 2.2 cm. Diameter: About 1.8 mm. Texture: Smooth, glabrous. Color: Close to 62D.

*Reproductive organs, fertile flowers.*—Stamens: Quantity per flower: About ten. Filament length: About 3 mm. Filament color: Close to 76D. Anther shape: Elliptic, elongated. Anther length: About 1.5 mm. Anther color: Close to 18C. Pollen amount: Moderate. Pollen color: Close to 19C. Pistils: Pistil quantity per flower: About three. Pistil length: About 1 mm. Stigma shape: Elliptic. Stigma color: Close to 19C. Style length: About 2 mm. Style color: Close to 156D. Ovary color: Close to 154C.

*Reproductive organs, sterile flowers.*—Stamens: Quantity per flower: About six. Filament length: About 2 mm. Filament color: Close to 85D. Anther shape: Elliptic, elongated. Anther length: About 1.2 mm. Anther color: Close to 164C. Pollen amount: Moderate. Pollen color: Close to 18C. Pistils: Pistil development has not been observed on sterile flowers.

*Seeds.*—Quantity per inflorescence: Numerous. Size: About 0.2 mm by 0.5 mm. Color: Close to 8D.

Disease/pest resistance: Plants of the new *Hydrangea* have been observed to be tolerant to Botrytis, Powdery Mildew, Fusarium, Pythium and Alternaria LeafBlight. Plants of the new *Hydrangea* have not been observed to be tolerant to pests or other pathogens common to *Hydrangea.*

Temperature tolerance: Plants of the new *Hydrangea* have been shown to be tolerant to temperatures ranging from about −3° C. to about 35° C.

It is claimed:

1. A new and distinct *Hydrangea* plant named 'Dancing Angel' as illustrated and described.

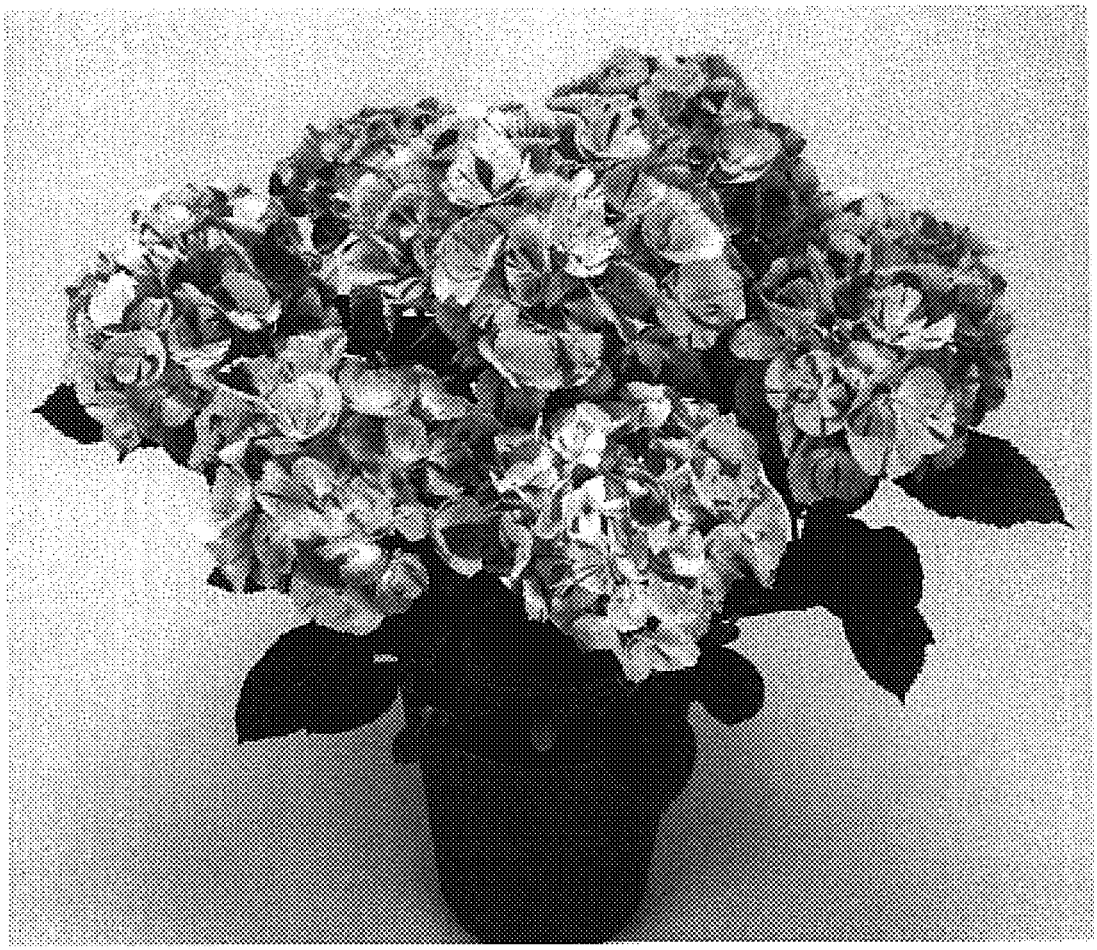

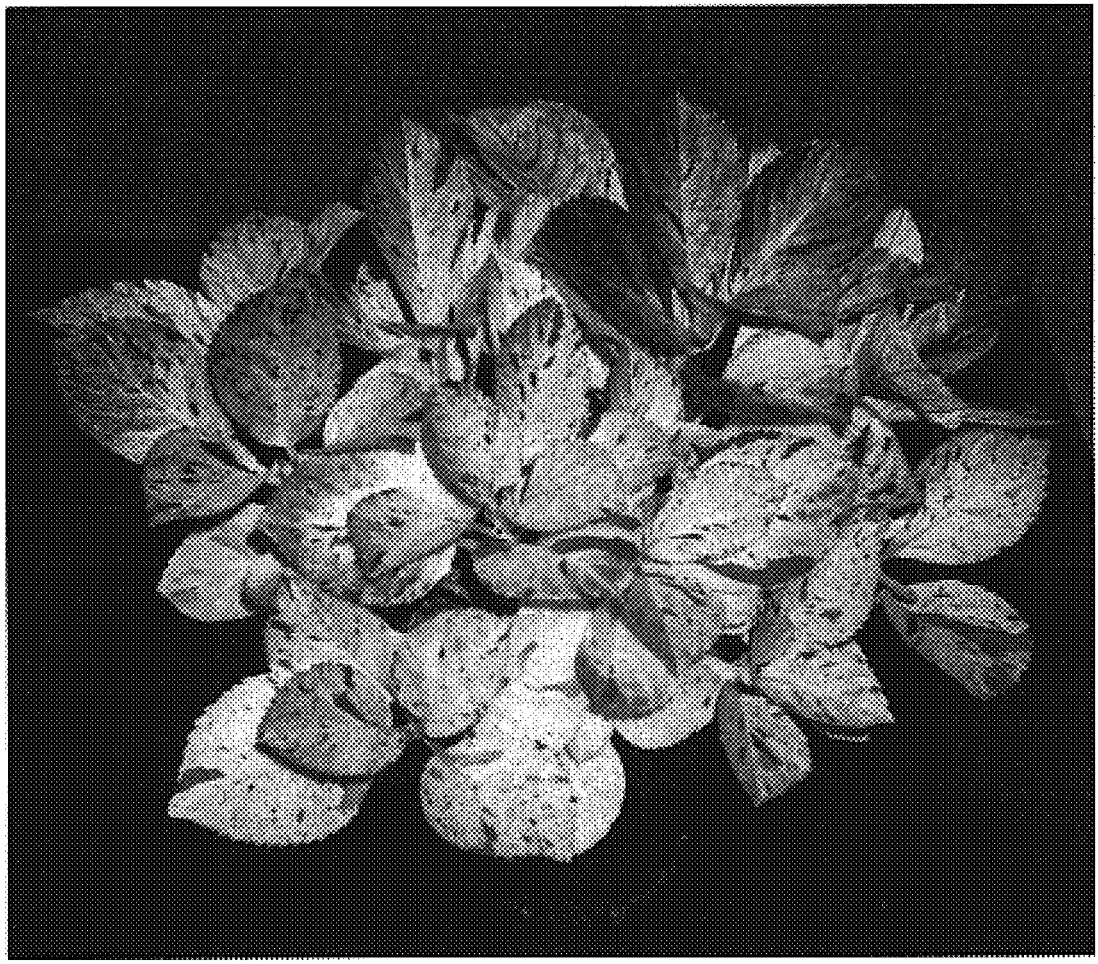

* * * * *